US010010071B2

United States Patent
Bungenstock et al.

(10) Patent No.: US 10,010,071 B2
(45) Date of Patent: Jul. 3, 2018

(54) LIQUID CONCENTRATE FOR THE PROTECTION OF COMPOSITIONS TO BE APPLIED TOPICALLY, AGAINST MICROBIAL ATTACK

(71) Applicant: L'AIR LIQUIDE, SOCIETE ANONYME POUR L'ETUDE ET L'EXPLOITATION DES PROCEDES GEORGES CLAUDE, Paris (FR)

(72) Inventors: Carsten Bungenstock, Hamburg (DE); Sarah Erichsen, Bad Oldesloe (DE); Sabine Herweg, Hamburg (DE); Sonja Luthje, Norderstedt (DE); Klaus Weber, Hamburg (DE)

(73) Assignee: L'AIR LIQUIDE SOCIETE ANONYME POUR L'ETUDE ET L'EXPLOITATION DES PROCEDES GEORGES CLAUDE, Paris (FR)

( * ) Notice: Subject to any disclaimer, the term of this patent is extended or adjusted under 35 U.S.C. 154(b) by 0 days.

(21) Appl. No.: 15/021,772

(22) PCT Filed: Sep. 22, 2014

(86) PCT No.: PCT/EP2014/070113
§ 371 (c)(1),
(2) Date: Mar. 14, 2016

(87) PCT Pub. No.: WO2015/044080
PCT Pub. Date: Apr. 2, 2015

(65) Prior Publication Data
US 2016/0227770 A1    Aug. 11, 2016

(30) Foreign Application Priority Data

Sep. 26, 2013  (DE) .................... 20 2013 104 382 U
Nov. 15, 2013  (EP) .................................... 13306562

(51) Int. Cl.
*A01N 31/02*    (2006.01)
*A61K 8/34*     (2006.01)
*A61K 8/67*     (2006.01)
*A61Q 19/00*    (2006.01)
*A01N 31/04*    (2006.01)

(52) U.S. Cl.
CPC ............. *A01N 31/02* (2013.01); *A01N 31/04* (2013.01); *A61K 8/34* (2013.01); *A61K 8/345* (2013.01); *A61K 8/678* (2013.01); *A61Q 19/00* (2013.01); *A61K 2800/10* (2013.01); *A61K 2800/522* (2013.01); *A61K 2800/524* (2013.01); *A61K 2800/5922* (2013.01)

(58) Field of Classification Search
None
See application file for complete search history.

(56) References Cited

U.S. PATENT DOCUMENTS 5,539,001 A    7/1996  Waldmann-Laue et al.

FOREIGN PATENT DOCUMENTS

| EP | 0 524 548 A1 | 1/1993 |
| JP | 2011 037786 A | 2/2011 |
| WO | 2006/045743 A1 | 5/2006 |
| WO | 2008061187 A1 | 5/2008 |

OTHER PUBLICATIONS

Sinerga, "FENICAP", Jul. 2012 (index date by Google), downloaded from "www.sinerga.it/letteratura-tecnica/AD/flyer_en_fenicap.pdf" on Mar. 2, 2017, 2 pages.*
International Search Report, dated Nov. 4, 2014, from corresponding PCT application.
EP Search Report, dated Mar. 18, 2014, from corresponding EP application.

* cited by examiner

*Primary Examiner* — Savitha M Rao
*Assistant Examiner* — Gregg Polansky
(74) *Attorney, Agent, or Firm* — Young & Thompson

(57) ABSTRACT

A liquid concentrate which includes:
  a) from 20 to 70% by weight of 3-phenylpropan-1-ol,
  b) from 10 to 50% by weight of 1,2-octanediol,
  c) from 15 to 60% by weight of 1,3-propanediol, and
  d) where necessary up to 2000 ppm of one or more antioxidants; and a composition for topical application, including such liquid concentrate.

10 Claims, No Drawings

LIQUID CONCENTRATE FOR THE PROTECTION OF COMPOSITIONS TO BE APPLIED TOPICALLY, AGAINST MICROBIAL ATTACK

The present invention relates to a liquid concentrate for the protection of compositions for topical application against microbial attack. In addition, the invention relates to products correspondingly equipped in a microbial manner.

Preservation agents for products to be applied topically, such as cosmetic agents, are known, but they frequently have drawbacks. Some of the active substances contained, for example formaldehyde releasing agents, parabens or isothiazolinones, are discussed critically. The use thereof in products to be applied topically is accordingly undesired. Organic acids can be used effectively only in products with a low pH value, and so the possibilities of use thereof are limited. These active substances are also in part allergens, such as for example benzyl alcohol with a poor storage stability as a raw material and in a concentrate, which in addition lead as a concentrate (and in part also in products equipped with them) to a perceptible odour.

Furthermore, the antimicrobial effects of aromatic alcohols (such as phenethyl alcohol or benzyl alcohol and combinations with phenoxyethanol and combinations with phenyl propanol) and of multivalent alcohols are known. EP 0 524 548 A1 discloses for example combinations of antimicrobially effective aromatic alcohols with antimicrobially effective 1,2- or 1,3-diols.

In addition, products with 1,2-octanediol (caprylyl glycol) to be applied topically can be equipped (preserved) in an antimicrobial manner. 1,2-Octanediol is an active substance which is frequently used in the preservation of cosmetic products, since it provides, in particular, an effectiveness against mould. Since the melting point of the diol is approximately 37° C., the raw material, however, is solid at room temperature and this makes it difficult to incorporate and meter into products. Liquid concentrates are therefore desired which have a high content of 1,2-octanediol and which can have a certain cold stability.

WO2008/061187 A1 discloses preservation agent compositions with a content of 1,3-propanediol, where necessary in a mixture with glycols. Mixtures of 1,3-propanediol with 1,2-octanediol and phenoxyethanol are further described in the examples. There are concerns about the use of phenoxyethanol, however, since this aromatic alcohol can allegedly be resorbed through the skin. In cosmetic products phenoxyethanol is therefore undesired, in particular for children and infants.

Furthermore, the product Fenicap® (Sinerga, Milan, Italy) is known which comprises 3-phenylpropan-1-ol (hydrocinnamic alcohol) and 1,2-octanediol. This concentrate (of from 35 to 45% 1,2-octanediol and from 65 to 55% by weight of 3-phenylpropan-1-ol) contains an advantageously high quantity of 1,2-octanediol, but is unsatisfactory with respect to its cold stability. This means that 1,2-octanediol can crystallize out during storage. The concentrate must therefore where necessary first be heated after transport at low temperatures so that it can then be added in a metered manner to a cosmetic product.

In addition, the product Dermosoft® OMP (Dr. Straetmans GmbH, Hamburg, Federal Republic of Germany) is known which comprises 2-methylpropanediol-1,3, 1,2-octanediol and 3-Phenylpropan-1-ol. On account of the low content of 1,2-octanediol (15%) and 3-Phenylpropan-1-ol (3%) the recommended application quantity amounts to from 2 to 4% by weight, whereas an application concentration of antimicrobial agents of 1±0.5% by weight is customary in the case of cosmetic products. In addition the recommended application concentration of up to 4% by weight introduces an undesirably high quantity of the solvent 2-methylpropanediol-1,3 into the product equipped with Dermosoft® OMP.

Furthermore, the product Sensiva® SC 10 of Schülke & Mayr GmbH (Norderstedt, Federal Republic of Germany) is known which comprises 70% of 1,2-octanediol and 30% by weight of 1-(2-ethylhexyl) glycerol. The concentrate thus contains a desirably high content of 1,2-octanediol and further comprises the skin nurturing and deodorizing 1-(2-ethylhexyl) glycerol. There is a need, however, for concentrates for the antimicrobial equipping of cosmetic products which do not necessarily contain 1-(2-ethylhexyl) glycerol ethers. In addition, the critical crystallization temperature of this liquid concentrate is approximately 15° C., and this leads to its frequently having to be heated by the customer to from 25 to 30° C. after transport in order to be able to incorporate it into a cosmetic product.

Consequently, the object of the present invention has been to make available a concentrate with a high content of 1,2-octanediol. The concentrate should also not have a tendency to become solid in the case of prolonged storage below 0° C. (such as below −5° C.). It should have an antimicrobial effect in the typical application concentration of 1.0±0.5% in cosmetic products, and it should protect the cosmetic product from attack by mould, yeast and bacteria. In addition, the concentrate should not contain further constituents undesired in the cosmetic products in large quantities. By way of example, the concentrate should not necessarily contain phenoxyethanol. In addition, the concentrate should not necessarily contain glycerol ethers, such as 1-(2-ethylhexyl) glycerol ethers.

It has now surprisingly been found that this object is attained by a liquid concentrate which comprises
 a) from 20 to 70% by weight of 3-phenylpropan-1-ol,
 b) from 10 to 50% by weight of 1,2-octanediol,
 c) from 15 to 60% by weight of 1,3-propanediol, and
 d) where necessary up to 2000 ppm of one or more antioxidants.

The liquid concentrate according to the invention attains the object specified above and is characterized in particular in that even over a prolonged period of time during storage at a low temperature, such as 0° C. or even −5° C., it has no tendency over a prolonged period of time towards the (complete) crystallization out of the 1,2-octanediol contained. In addition, with the constituents a) to c) the concentrate contains predominantly natural or nature-identical substances and can, if this is desired, be protected for example with vitamin E as an antioxidant against the formation of undesired degradation products. In this way, no undesired constituents are introduced by concentrates according to the invention in the antimicrobial equipping of products for topical application (such as for example medical creams and cosmetic products).

In a preferred embodiment the concentrate comprises the constituents a) to c) and where necessary d), i.e. in this preferred embodiment no further constituents are contained in the concentrate according to the invention in addition to the constituents a) to c) and where necessary d).

In a further preferred embodiment the concentrate according to the invention comprises a) from 30 to 60% by weight of 3-phenylpropan-1-ol, preferably from 40 to 50% by weight, such as for example 45% by weight.

It is further preferred for the concentrate to comprise b) from 15 to 40% by weight of 1,2-octanediol, preferably from 20 to 30% by weight, such as for example 25% by weight.

In addition, it is preferred for the concentrate according to the invention to comprise c) from 20 to 45% by weight of 1,3-propanediol, preferably from 25 to 35% by weight, such as for example 30% by weight.

Liquid concentrates according to the invention contain where necessary d) up to 2000 ppm of one or more antioxidants. It is preferred for the antioxidant to be selected from phenol compounds such as 3-tert-butyl-4-hydroxyanisole, 2,6-di-tert-butyl-p-cresol, dodecylgallate, pyrogallate, tocopherol (for example vitamin E) and the derivatives thereof (for example vitamin E acetate), as well as mixtures of these antioxidants, preferably vitamin E and the derivatives thereof, and in a particularly preferable manner vitamin E.

In addition, it is preferable for the quantity of the component d), i.e. the total quantity of the one or more antioxidants, to amount to from 20 to 400 ppm, preferably from 50 to 300 ppm, in particular from 80 to 200 ppm, such as for example 100 ppm, relative to the weight of the concentrate.

It is preferable for the liquid concentrate according to the invention not to comprise glycerol either, and in particular not 1-(2-ethylhexyl) glycerol ether. In addition, it is preferable for the concentrate according to the invention not to comprise phenoxyethanol.

In a first particularly preferred embodiment the concentrate comprises
a) from 40 to 50% by weight (such as for example 45% by weight) of 3-phenylpropan-1-ol,
b) from 20 to 30% by weight (such as for example 25% by weight) of 1,2-octanediol,
c) from 25 to 35% by weight (such as for example 30% by weight) of 1,3-propanediol and
d) where necessary from 50 to 300 ppm (in particular from 80 to 200 ppm, such as for example 100 ppm) of one or more antioxidants.

In a second particularly preferred embodiment the concentrate consists of
a) from 40 to 50% by weight (such as for example 45% by weight) of 3-phenylpropan-1-ol,
b) from 20 to 30% by weight (such as for example 25% by weight) of 1,2-octanediol,
c) from 25 to 35% by weight (such as for example 30% by weight) of 1,3-propanediol and
d) where necessary from 50 to 300 ppm (in particular from 80 to 200 ppm, such as for example 100 ppm) of one or more antioxidants.

With concentrates according to the invention it is possible for leave-on and rinse-off formulations to be preserved (i.e. equipped in an antimicrobial manner) for medical purposes or for cosmetic purposes. Preservation agents which contain phenoxyethanol can be replaced. Since the constituents necessarily prescribed in the concentrate according to the invention display further advantageous properties in the topical application, i.e. they are multifunctional, it is also possible for products equipped in an antimicrobial manner according to the invention to be recommended as products free from preservation agents.

The invention further relates to a composition for topical application, which comprises from 0.2 to 3.0% by weight of the concentrate, preferably from 0.3 to 2.0% by weight, in particular from 0.5 to 1.5% by weight. It is preferable for the product to be a cream.

The concentrates according to the present invention are associated with the following advantages:
good cold stability with high concentration of active substances
liquid variant of 1,2-octanediol
very good effectiveness with low application concentration
improved effectiveness as compared with the individual components
improved odour with respect to an equally high concentration of 3-phenylpropan-1-ol
improved skin compatibility with respect to the concentration of 1,2-octanediol necessary for equally good effectiveness
improved storage stability by the addition of antioxidants is possible, thus preventing possible undesired degradation products even in products to be applied topically
high proportion of natural (1,3-propanediol) or nature-identical (3-phenylpropan-1-ol) components
free from active substances discussed as being disadvantageous, such as for example bronopol, parabens, isothiazolinones and formaldehyde releasing agents
good effectiveness even with relatively high pH-values (pH-value>7)
the 1,3-propanediol contained has, also has skin compatible properties as well as an effectiveness portion Advantages of 3-Phenylpropan-1-ol:
storage stable and less odour intensive than for example phenethyl alcohol
pH-neutral
pH-stable
high thermal and cold stability (in heat, for example when stored at 40° C., significantly lower tendency to oxidative breakdown than benzyl alcohol or phenethyl alcohol, caused by the melting point, approximately −18° C., tends to crystallize less rapidly than phenoxyethanol with approximately +14° C.)
good antimicrobial effectiveness, in particular also in the fungicidal field
nature-identical.

Advantages of 1,2-octanediol:
good effectiveness, in particular as a booster, in particular also in the fungicidal field
pH-neutral
pH-stable.

Advantages of 1,3-propanediol:
nature-identical
skin compatible and moisturizing properties
solubilizer
antimicrobial booster
crystallization inhibitor.

The advantages of the present invention are evident in particular from the examples. Unless indicated otherwise, percentages relate to the weight.

EXAMPLE 1

Storage Stability at Low Temperature

The following concentrates $C_1$, $C_2$, $C_2^*$, $C_A$ were formulated (Table 1):

TABLE 1

| | Concentrates | | | |
|---|---|---|---|---|
| Constituents | $C_1$ | $C_2$ | $C_2^*$ | $C_A$ |
| 1,3-propanediol | 20.0 wt % | 30.0 w % | 30.0 w % | 0 w % |
| 1,2-octanediol | 30.0 w % | 25.0 w % | 25.0 w % | 35.7 w % |
| 3-phenyl-propan-1-ol | 50.0 w % | 45.0 w % | 45.0 w % | 64.3 w % |
| Vitamin E | 0 | | 100 ppm | 100 ppm |

Concentrate $C_2^*$ is based upon concentrate $C_2$ and additionally contains 100 ppm of vitamin E as the sole further constituent.

The cold stability of the concentrates $C_1$, $C_2$ and $C_2^*$ according to the invention and $C_A$ according to the state of the art, were tested in a 30 ml screw lid glass (see Tables 2 to 4):

TABLE 2

Short term cold stability test without inoculation

| Storage | $C_1$ 24 hours | $C_2^*$ 24 hours |
|---|---|---|
| +5° C. | clear | Clear |
| −5° C. | clear | Clear |

TABLE 3

Long term cold stability test at −5° C. without inoculation

| | $C_1$ | $C_2$ | $C_2^*$ |
|---|---|---|---|
| Zero value | clear colourless liquid | clear colourless liquid | clear colourless liquid |
| 3 months | clear colourless liquid | clear colourless liquid | clear colourless liquid |

Since a delayed crystallization takes place in part in the case of 1,2-octanediol, the concentrates were inoculated in the cold (Table 4)

TABLE 4

Short term cold stability test with inoculation with seed crystals

| | $C_1$ | | $C_2$ | |
|---|---|---|---|---|
| Storage | 24 hours | 48 hours | 24 hours | 48 hours |
| +5° C. | Clear | clear | clear | Clear |
| −5° C. | One third of the concentrate is crystallized | concentrate completely crystallized out | inoculation crystals still present, no further crystallization | inoculation crystals still present, no further crystallization |

TABLE 4

Short term cold stability test with inoculation with seed crystals

| | $C_2^*$ | | $C_A$ | |
|---|---|---|---|---|
| Storage | 24 hours | 168 hours | 24 hours | 48 hours |
| −5° C. | Clear solution | Clear solution | Several crystallisation points | One half of the volume is crystallized |

The cold stability tests show that the concentrates $C_1$, $C_2$, $C_2^*$ according to the invention have a better storage stability in the cold than the concentrate $C_A$ according to the state of the art has.

The presence of 1,3-propanediol, in the preservative composition thus generates the stabilizing effect at low temperature.

EXAMPLE 2

Determination of the Preservation Effect (Koko Test)

The test described below is carried out in order to determine the preservation effect in cosmetic formulations.

Principle

The effectiveness of chemical preservation agents with respect to the in-can preservation for cosmetics formulations is to be checked with the aid of the method described. To this end, in various test charges the preservation agents to be tested are added in various concentrations to the non-preserved samples. A current germ load is achieved by periodic inoculation of the test charges. Parallel to the inoculation, smears of the original charges are carried out immediately beforehand in each case. An evaluation is carried out with reference to the microbial growth of the smears. The longer of period of time until the first occurrence of microbial growth, the more effective a preservation agent is.

Performance 25 g of the cosmetic product to be tested are weighed in each case into wide-necked bottles with a screw closure (LDPE). The preservation agents to be tested are added in separate charges in each case in their application concentrations. A non-preserved sample acts in each case as a growth control. Two days after the addition of the preservation agents the samples are infected with 0.1 ml of an inoculation solution consisting of the test organisms listed below. The inoculation solution has a titre of from approximately $10^8$ to $10^9$ germs/ml (Table 5).

TABLE 5

| Bacteria | Gram positive | | *Staphylococcus aureus* | ATCC 6538 |
|---|---|---|---|---|
| | | | *Kocuria rhizophila* | ATCC 9341 |
| | Gram negative | Enterobacteria | *Enterobacter gergoviae* | ATCC 33028 |
| | | | *Escherichia coli* | ATCC 11229 |
| | | | *Klebsiella pneumonia* | ATCC 4352 |
| | | Pseudomonads | *Pseudomonas aeruginosa* | ATCC 9027 |
| | | | *Pseudomonas fluorescens* | ATCC 17397 |
| | | | *Pseudomonas putida* | ATCC 12633 |
| Yeast | | | *Candida albicans* | ATCC 10231 |
| Mould | | | *Aspergillus brasiliensis* | ATCC 16404 |
| | | | *Penicillium pinophilum* | ATCC 36839 |

The test charges are spread in sequence once per week on agar plates (casein peptone-soya bean flour peptone agar (CSA) for bacteria and sabouraud dextrose agar (SA) for yeasts and mould) and are then inoculated. The first smear (sterility test) is carried out both on uninhibited (TLSH) and on inhibited breeding grounds, in order to cover all the initial contamination as far as possible. The evaluation of the microbial growth of the smears is carried out after a three-day incubation at 25° C. Negative smears are observed for a further two days as a precaution and are evaluated again. The evaluation of the preservation effect of the individual product concentrations is carried out in a semiquantitative method over the growth of the individual smears.

−=growth free ++=moderate growth
+=weak growth +++=strong growth

The growth is differentiated in accordance with bacteria, yeasts and moulds. The test is carried out for a maximum of six weeks, i.e. over six inoculation cycles, and is discontinued after strong growth (+++) a number of times.

Evaluation of the Results

The sample is well preserved according to criterion A if it survives under the laboratory conditions specified above for a period of time of six weeks without bacterial attack of the sample charges, i.e. no microbial growth is capable of being demonstrated even after the sixth inoculation. On the basis of many years' experience with this testing method a microbiological stability of over 30 months recommended for cosmetic products can be deduced from this.

If the sample displays a weak microbial growth (+) during the six inoculation cycles, then the sample meets criterion B.

A B criterion can constitute an adequate degree of preservation when the microbiological risk analysis has control factors independent of the formulation. This could be for example the use of a package with a pump instead of a can and/or high demands made upon good manufacturing practice (GMP).

Results of the KoKo Test

The concentrates 2 and 2* were tested in an O/W cream, the constituents and quantities of which are listed in Table 6:

TABLE 6

Constituents of a test cream O/W

| | % by weight |
|---|---|
| Phase A (aqueous phase) | |
| Water | 75.0 |
| Glycerol (85%) | 2.3 |
| NaOH (45%) | 0.2 |
| Phase B (fatty phase) | |
| Paraffinum Liquidum | 6.0 |
| Dimethicones | 5.0 |
| Stearic acid | 4.0 |
| Cetyl alcohol | 3.0 |
| Glyceryl stearate/PEG 30-stearate | 3.0 |
| Octyl palmitate | 1.5 |

The constituents of phase A were heated to 80° C. The constituents of phase B were heated to 80° C. in a separate container. Phase B was then introduced into phase A with slight mixing (approximately 400 min$^{-1}$), and homogenization was then carried out. Cooling to room temperature was carried out with stirring (approximately 300 min$^{-1}$), in order to obtain the O/W cream.

Different quantities of the concentrates 2 and 2* according to the invention were added to this O/W cream (pH value 5.5). The results are set out below in Table 7.

TABLE 7

| | | pH | Start | 1 w. | 2 w. | 3 w. | 4 w. | 5 w. | 6 w. |
|---|---|---|---|---|---|---|---|---|---|
| 1 | Blank value | 5.5 | — | +++ SHB | +++ SHB | ./. | | | |
| 2 | 1.0% concentrate 2* | 5.5 | — | — | — | — | — | — | — |
| 3 | 1.0% concentrate 2 | 5.5 | — | — | — | — | — | — | — |
| 4 | 1.5% concentrate 2* | 5.5 | — | — | — | — | — | — | — |
| 5 | 1.5% concentrate 2 | 5.5 | — | — | — | — | — | — | — | w = week(s)

The results show that a typical cream is preserved by concentrates according to the invention even in an application quantity of 1.0% by weight.

EXAMPLE 3

Germ Count Reduction Test

Hereinabove O/W Cream samples (25 cm$^3$) were respectively added with the following concentrates:
1 w % of concentrate $C_2$, (Sample 1)
0.75 w % of concentrate $C_B$ (40 w % 1,3-propanediol+60 w % 3-phenyl-1-propanol) (Sample 2)
0.75 w % of concentrate $C_C$ (40 w % 1,3-propanediol+60 w % 1,2-octanediol) (Sample 3)
0.3 w % of concentrate $C_D$ (100 w % 1,3-propanediol) (Sample 4)
0.45 w % concentrate $C_E$ (100 w % 3-phenyl-1-propanol) (Sample 5)
0.25 w % concentrate $C_F$ (100 w % 1,2-octanediol) (Sample 6)

After inoculation of various germs with 0.1 cm$^3$ microorganism suspensions, the germ reduction is evaluated along the time for each samples and compared to a sample of said O/W cream without preservative (Sample T).

The results as shown in the following table 8, support the efficiency of the ternary composition according to the invention.

TABLE 8

| Exposure time | 3 h | 6 h | 24 h | 72 h | 168 h |
|---|---|---|---|---|---|
| *Staphylococcus aureus* ATCC 6538 | | | | | |
| Sample T | C | C | C | C | C |
| Sample 1 | ++++ | ++ | + | − | − |
| Sample 2 | C | C | ++++ | ++++ | +++ |
| Sample 3 | C | C | C | C | +++ |
| Sample 4 | C | C | ++++ | ++++ | +++ |
| Sample 5 | C | C | C | C | +++ |
| Sample 6 | C | C | C | C | +++ |
| *Pseudomonas aeruginosa* ATCC 9027 | | | | | |
| Sample T | C | C | C | C | C |
| Sample 1 | − | − | − | − | − |
| Sample 2 | + | + | − | − | − |
| Sample 3 | ++++ | ++ | + | − | − |
| Sample 4 | C | C | C | C | C |
| Sample 5 | − | − | − | − | − |
| Sample 6 | ++ | + | − | − | − |
| *Candida albicans* ATCC 10231 | | | | | |
| Sample T | C | ++++ | ++++ | ++++ | ++++ |
| Sample 1 | +++ | +++ | − | − | − |
| Sample 2 | +++ | +++ | + | + | + |
| Sample 3 | ++++ | ++ | + | − | − |
| Sample 4 | +++ | +++ | +++ | + | + |
| Sample 5 | +++ | +++ | +++ | + | + |
| Sample 6 | ++++ | +++ | +++ | + | + |
| *Aspergillus brasiliensis* ATCC 16404 | | | | | |
| Sample T | C | C | C | C | C |
| Sample 1 | C | +++ | ++ | + | − |
| Sample 2 | C | C | C | C | ++++ |
| Sample 3 | C | C | C | C | C |
| Sample 4 | C | C | C | C | C |
| Sample 5 | C | C | C | C | ++++ |
| Sample 6 | C | C | C | C | C |

−: No growth (<100 germs/ml)
+: Slight growth (around 100 germs/ml)
++: Moderate growth (around 1,000 germs/ml)
+++: Heavy growth (around 10,000 germs/ml)
++++: Massive growth (around 100,000 germs/ml)
C: Surface covered (around 1,000,000 germs/ml)

The invention claimed is:
1. A liquid concentrate, which comprises
from 40% to 50% by weight of 3-phenylpropan-1-ol,
from 20% to 30% by weight of 1,2-octanediol, and
from 25% to 35% by weight of 1,3-propanediol.

2. The concentrate according to claim 1, which further comprises at least one antioxidant selected from the group consisting of 3-tert-butyl-4-hydroxyanisole, 2,6-di-tert-butyl-p-cresol, dodecylgallate, pyrogallate, tocopherol and tocopherol acetate.

3. The concentrate according to claim 2, wherein the antioxidant is vitamin E.

4. The concentrate according to claim 1, which further comprises from 80 ppm to 200 ppm of one or more antioxidants.

5. A composition for topical application, which comprises from 0.2 to 3.0% by weight of the concentrate according to claim 1.

6. The concentrate according to claim 1, which further comprises up to 2000 ppm of one or more antioxidants.

7. A liquid concentrate, which consists of
From 40 to 50% by weight of 3-phenylpropan-1-ol,
From 20 to 30% by weight of 1,2-octanediol, and
From 25 to 35% by weight of 1,3-propanediol.

8. A liquid concentrate, which consists of
From 40 to 50% by weight of 3-phenylpropan-1-ol,
From 20 to 30% by weight of 1,2-octanediol,
From 25 to 35% by weight of 1,3-propanediol, and
80 to 200 ppm of Vitamin E.

9. A composition formulated for topical application, which comprises from 0.2 to 3.0% by weight of the concentrate according to claim 7.

10. A composition formulated for topical application, which comprises from 0.2 to 3.0% by weight of the concentrate according to claim 8.

* * * * *